United States Patent [19]

Chen et al.

[11] Patent Number: 5,952,528
[45] Date of Patent: Sep. 14, 1999

[54] PROCESS FOR ENHANCING THE OPTICAL PURITY

[75] Inventors: Cheng Yi Chen, Colonia; Edward J. J. Grabowski; Paul J. Reider, both of Westfield; Lushi Tan, Edison; Richard D. Tillyer, Cranford, all of N.J.

[73] Assignee: Merck & Co., Inc., Rahway, N.J.

[21] Appl. No.: 09/145,667

[22] Filed: Sep. 2, 1998

Related U.S. Application Data

[60] Provisional application No. 60/057,891, Sep. 3, 1997, and provisional application No. 60/096,529, Aug. 14, 1998.

[51] Int. Cl.[6] .................................................. C07C 209/88
[52] U.S. Cl. ............................................................ 564/425
[58] Field of Search ............................................ 564/425

[56] References Cited

U.S. PATENT DOCUMENTS 3,497,517  2/1970  Ettingen et al. .
4,085,138  4/1978  Whitney .
5,679,857  10/1997  Hijiya et al. ............................ 564/304

FOREIGN PATENT DOCUMENTS 0 582 455 A1  3/1993  European Pat. Off. .

OTHER PUBLICATIONS

Ryoichiro, N., et al., Chem. Abstract, Abstract No. 127:95076, 1997.

*Primary Examiner*—Brian M. Burn
*Attorney, Agent, or Firm*—Valerie J. Camara; Mark R. Daniel

[57] ABSTRACT

A process for enhancing the purity of 2R-[1-hydroxy-1-trifluoromethyl-3-cyclopropylpropyn-2-yl]-4-chloroaniline comprising the formation of an acid addition salt which is capable of rejecting the racemate in the selected organic solvent.

9 Claims, No Drawings

PROCESS FOR ENHANCING THE OPTICAL PURITY

This application claims benefit of Provisional Appl. 60/057,891 filed Sep. 3, 1997 and Provisional Appl. 60/096,529 filed Aug. 14, 1998.

BACKGROUND OF THE INVENTION

A key step in the synthesis of the reverse transcriptase inhibitor, (−)-6-chloro-4-cyclopropylethynyl-4-trifluoromethyl-1,4-dihydro-2H-3,1-benzoxazin-2-one, also known as DMP-266, is the chiral addition to the 2-trifluoromethylcarbonyl-4-chloroaniline to give desired enantiomer of the amino alcohol in optically pure form.

The synthesis of DMP-266 and structurally similar reverse transcriptase inhibitors are disclosed in U.S. Pat. No. 5,519,021 and the corresponding PCT International Patent Application WO 95/20389, which published on Aug. 3, 1995. Additionally, the asymmetric synthesis of an enantiomeric benzoxazinone by a highly enantioselective acetylide addition and cyclization sequence that has been described by Thompson, et al., Tetrahedron Letters 1995, 36, 8937–8940, as well as the PCT publication, WO 96/37457, which published on Nov. 28, 1996.

Additionally, several applications have been filed which disclose various aspects of the synthesis of (−)-6-chloro-4-cyclopropylethynyl-4-trifluoromethyl-1,4-dihydro-2H-3,1-benzoxazin-2-one including: 1) a process for making the chiral alcohol, U.S. Ser. No. 60/035,462, filed Jan. 14, 1997; 2) the chiral additive, U.S. Ser. No. 60/034,926, filed Jan. 10, 1997, U.S. Ser. No. 60/042,021, filed Apr. 17, 1997, U.S. Ser. No. 60/045,167, filed Apr. 30, 1997; 3) a cyclization reaction, U.S. Ser. No. 60/037,059, filed Feb. 12, 1997; 4) the anti-solvent crystallization procedure, U.S. Ser. No. 60/037,385 filed Feb. 5, 1997 and U.S. Ser. No. 60/042,807 filed Apr. 8, 1997; 5) a zinc-catalyzed enantioselective addition U.S. Ser. No. 60/046,713 filed May 16, 1997; and 6) a process for preparing cyclopropylacetylene, U.S. Ser. No. 60/047,692 filed May 23, 1997.

The instant invention discloses an efficient method for enhancing the optical purity of the amino alcohol:

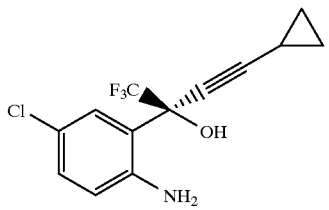

The instant method allows one to enhance the optical purity of the amino alcohol regardless of the synthetic route used to make the amino alcohol. The previous methods used the protection of the amino group as a means for enhancing the enantiomeric excess of the desired R-amino alcohol. In the most recent process developments the protection deprotection sequence has been eliminated necessitating a means by which the enantiomeric excess amino alcohol could be upgraded.

SUMMARY OF THE INVENTION

The instant invention relates to the process for enhancing the enantiomer excess of the R-amino alcohol comprising forming the acid addition salt with an acid having a pKa of less than or equal to 3, and selectively crystallizing the R-amino alcohol acid addition salt from the racemic mixture using the appropriate organic solvent so as to enhance the optical purity.

DETAILED DESCRIPTION OF THE INVENTION

The instant invention relates to a process for enhancing the optical purity of the R-amino alcohol of formula:

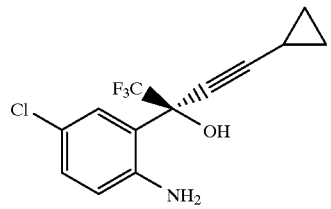

comprising the steps of:

(a) adding slowly an acid solution or gas to a solution of the amino alcohol in an organic solvent to form a slurry of the acid addition salt of the amino alcohol;

(b) concentrating the slurry of the amino alcohol acid addition salt of the amino alcohol;

(c) flushing the concentrated slurry of the amino alcohol acid addition salt with organic solvent to adjust the solvent composition;

(d) aging the slurry of the amino alcohol acid addition salt at ambient temperature for about 2 hours to about 24 hours;

(e) filtering the aged slurry of the amino alcohol acid addition salt to isolate a wetcake of the amino alcohol acid addition salt;

(f) washing the wetcake of the amino alcohol acid addition salt with cold organic solvent; and (g) drying the wetcake of the amino alcohol acid addition salt to isolate the amino alcohol acid addition salt as a solid with enhanced optical purity.

The acid solution or gas is defined as an acid having a pKa of less than or equal to 3, and preferably a pKa of less than or equal to 1. Examples of the acid useful in the instant process is HX, wherein X represents halide (Cl, Br, I, or F), $H_2SO_4$, trifluoroacetic acid (TFA), trichloroacetic acid, $RSO_3H$, wherein R represents $(C_1-C_6)$-alkyl, $(C_2-C_6)$-alkenyl, $(C_2-C_6)$-alkynyl, aryl which is defined as phenyl or naphthyl and heteroaryl which is defined as 5 or 6-membered ring substituted with one or two heteroatoms selected from O, S, N, and $(C_1-C_6)$-alkyl, $(C_2-C_6)$-alkenyl, $(C_2-C_6)$-alkynyl, aryl or heteroaryl can be substituted or unsubstituted with one, two or three substituents selected from the group consisting of: Br, Cl, F, I, $(C_1-C_6)$-alkyl, $(C_2-C_6)$-alkenyl, $(C_2-C_6)$-alkynyl, $(C_1-C_6)$-alkoxy, cyano, nitro, hydroxy, CHO, $CO_2H$, $SO_3H$, $COC_1-C_6$-alkyl, $CO_2C_1-C_6$-alkyl, $CONR^1R^2$, $NR^1R^2$, $NR^1COC_1-C_6$-alkyl, wherein $R^1$ and $R^2$ are independently defined as: halo (Cl, Br, F, I), $CF_3$, CN, $NO_2$, $NH_2$, $NH(C_1-C_6$-alkyl), $N(C_1-C_6$-alkyl)$_2$, $CONH_2$, $CONH(C_1-C_6$-alkyl), $CON(C_1-C_6$-alkyl)$_2$, $NHCONH_2$, $NHCONH(C_1-C_6$-alkyl), $NHCON(C_1-C_6$-alkyl)$_2$, $CO_2-C_1-C_6$-alkyl, $C_1-C_6$-alkyl, $C_2-C_6$-alkenyl, $C_2-C_6$-alkynyl, $C_3-C_7$-cycloalkyl, or $C_1-C_6$-alkoxy, such that $C_1-C_6$-alkyl is unsubstituted or substituted with aryl, aryl is defined as phenyl or naphthyl, unsubstituted or substituted with $C_1-C_6$-alkyl, $C_1-C_6$-alkoxy, $NO_2$, or halo (Cl, Br, F, I). Examples of $RSO_3H$ include but are not limited to 1,5-naphthalenedisulfonic acid, p-toluenesulfonic acid (p-TsOH), CH₃SO₃H, triflic acid (CF₃SO₃H), and camphorsulfonic acid. A solution of the organic acid would most frequently be added to a solution of the amino alcohol, however the gaseous acid can be bubbled inot the reaction. The solvent used to dissolve the acid would be water, or an alkanol, such as methanol, ethanol, isopropanol. The preferred acids are: HCl, HBr, H₂SO₄, 1,5-naphthalenedisulfonic acid, and p-toluenesulsonic acid. The most preferred acids are: HCl and HBr.

Examples of the organic solvents are: isopropyl acetate (IPAc), ethyl acetate (EtOAc), toluene, methyl t-butyl ether (MTBE), acetonitrile (ACN), tetrahydrofuran (THF), isopropanol (IPA) and hydrocarbon solvents such as hexanes, pentanes, heptanes, etc. Also included within the definition of organic solvent is a mixture of said solvents.

An embodiment of the process for enhancing the optical purity of the R-amino alcohol

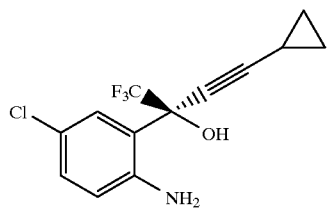

wherein the acid solution or gas and organic solvent are: HCl and isopropyl acetate, HBr and isopropyl acetate or HBr and a toluene-tetrahydrofuran mixture.

The slurry is concentrated and flushed with additional organic solvent to adjust the solvent composition so as to lower the concentration of the amino alcohol from about 10% to about 2% of the R-amino alcohol in the solvent.

The slurry is aged for about 2 hours to about 36 hours. The wetcake of the amino alcohol acid addition salt is washed with a bed volume of organic solvent of less than or equal to 20% of the original volume of organic solvent.

The term inert atmosphere is understood to be an atmosphere of argon or nitrogen, preferrably nitrogen. Ambient temperature is understood to represent a temperature range of from 20° C. to about 35° C.

The R-amino alcohol (2R-[1-hydroxy-1-trifluoromethyl-3-cyclopropylpropyn-2-yl]-4-chloroaniline) can be prepared according to the procedures described herein, as well as using any other known methods for its preparation. This invention is a method for enhancing the optical purity of this key intermediate in the synthesis of (−)-6-chloro-4-cyclopropylethynyl-4-trifluoromethyl-1,4-dihydro-2H-3,1-benzoxazin-2-one. The prior methods for making this key intermediate involved protecting the amine with an amine protecting group, such as p-nitrobenzyl, p-methoxybenzyl, and trityl group, and enhancing the optical purity of this protected intermediate. See Scheme 1. The zinc coupling procedure used to prepare the amino alcohol has eliminated the protection-deprotection sequence of steps and required the development of a method for enhancing the optical purity of the R-amino alcohol. However, this procedure as noted earlier can be employed to enhance the optical purity of this compound regardless of how it was made.

The compounds of the present invention have asymmetric centers and this invention includes all of the optical isomers and mixtures thereof.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkenyl and Alkynyl" is intended to include hydrocarbon chains of a specified number of carbon atoms of either a straight- or branched-configuration and at least one double or triple bond, which may occur at any point along the chain. Examples of "alkenyl" include ethenyl, propenyl, butenyl, pentenyl, dimethyl pentenyl, and the like, and includes E and Z forms, where applicable. Examples of "alkynyl" include ethynyl, propynyl, butynyl, pentynyl, and dimethyl pentynyl. "Halogen", as used herein, means fluoro, chloro, bromo and iodo.

The term "aryl" is defined as a phenyl or naphthyl ring which is optionally substituted with the substituents listed above at any available carbon atoms. The aryl may also be substituted with a fused 5-, 6-, or 7-membered ring containing one or two oxygens and the remaining ring atoms being carbon, the fused 5-, 6-, or 7-ring being selected from the group consisting of: dioxolanyl, dihydrofuranyl, dihydropyranyl, and dioxanyl.

The term "heteroaryl" as utilized herein is intended to include the following a 5 or 6-membered ring substituted with one or two heteroatoms selected from O, S, N, and is unsubstituted or substituted with one, two or three substituents selected from the group consisting of: Br, Cl, F, I, (C₁–C₆)-alkoxy, cyano, nitro, hydroxy, CHO, CO₂H, COC₁–C₆-alkyl, CO₂C₁–C₆-alkyl, CONR¹R², NR¹R², NR¹COC₁–C₆-alkyl, any two adjacent substituents can be joined to form a 5-, 6- or 7-membered fused ring said ring containing 1 or 2 oxygen atoms and the remainder carbon atoms, or any two adjacent substituents can be joined together to form a benzo-fused ring. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, pyrazinyl, pyridazinyl, pyridinyl, pyrimidinyl, and pyrrolyl which are substituted or unsubstituted as defined above.

Scheme 1 outlines the key steps in the synthesis of (−)-6-chloro-4-cyclopropylethynyl-4-trifluoromethyl-1,4-dihydro-2H-3,1-benzoxazin-2-one (DMP-266). The chiral addition step allows for the enantioselective addition of the cyclopropylacetylide across the trifluoromethylketone of 1. The p-methoxybenzyl (PMB)-protected amino alcohol, 2, produced is then deprotected to give the amino alcohol, 3. The amino alcohol is then cyclized using a chloroformate and base to give DMP-266.

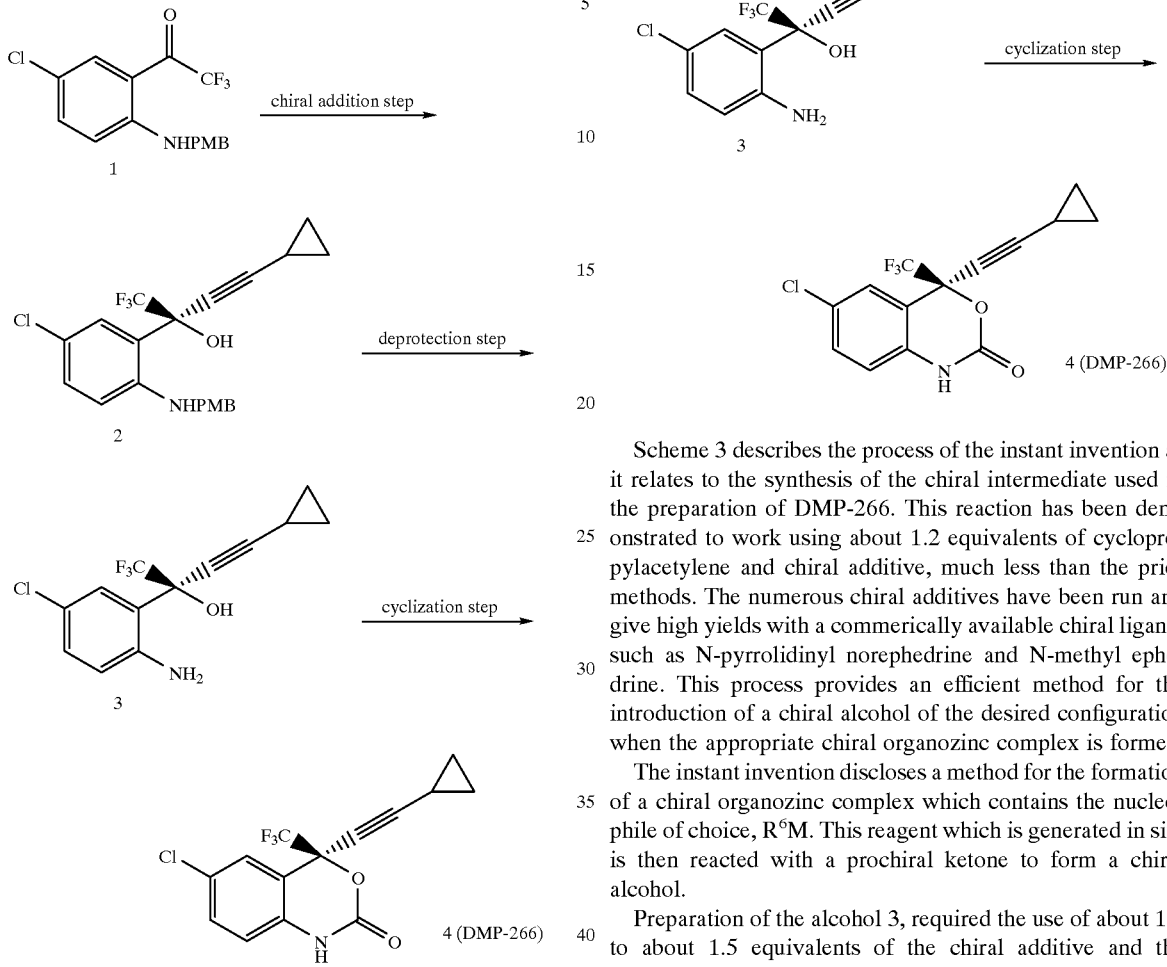

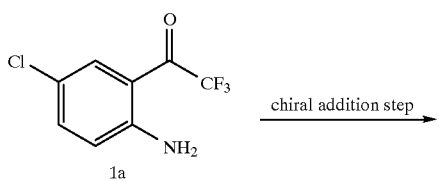

Scheme 2 outlines the preparation of DMP-266 using the process of the present invention which is a chiral addition reaction. The new chiral addition reaction allows for the elimination of the protection-deprotection sequence as outlined in Scheme 1.

Scheme 3 describes the process of the instant invention as it relates to the synthesis of the chiral intermediate used in the preparation of DMP-266. This reaction has been demonstrated to work using about 1.2 equivalents of cyclopropylacetylene and chiral additive, much less than the prior methods. The numerous chiral additives have been run and give high yields with a commerically available chiral ligand, such as N-pyrrolidinyl norephedrine and N-methyl ephedrine. This process provides an efficient method for the introduction of a chiral alcohol of the desired configuration when the appropriate chiral organozinc complex is formed.

The instant invention discloses a method for the formation of a chiral organozinc complex which contains the nucleophile of choice, $R^6M$. This reagent which is generated in situ is then reacted with a prochiral ketone to form a chiral alcohol.

Preparation of the alcohol 3, required the use of about 1.0 to about 1.5 equivalents of the chiral additive and the nucleophile; or preferably about 1.2 equivalents of the chiral additive and about 1.0 equivalent of the nucleophile.

The reaction can be run at a temperature of about −78° C. to about 70° C., and preferably at a temperature of about −20° C. to about 60° C., as opposed to the low temperature conditions (−65° C.) required by the prior method. The dialkylzinc is typically added at a temperature of about −20° C. to about 0° C. The second additive is typically added at about ambient temperature, the mixture is then heated to about 60° C. to effect the formation of the chiral organozinc complex. The organometallic reagent ($R^6M$) is added to the chiral organozinc complex at about room temperature. To this chiral nucleophile-organozinc complex is added the prochiral ketone at room temperature.

A preferred procedure involves the slow addition of a solution of the dialkylzinc to a solution of the solution of the chiral additive and second additive so as to maintain the reaction temperature at between 0° C. and 30° C. After about one hour an organometallic reagent, such as chloromagnesium cyclopropylacetylide, is prepared and added to the chiral organozinc complex. Then, the ketoaniline is added at about −10° C. to this chiral nucleophile-organozinc complex solution. The reaction is stirred for about 35 hours at about 0° C. to about −10° C., warmed to room temperature, stirred for about 3 hours, and then quenched with a base.

Additionally, this method has been demonstrated to provide a catalytic method for making the desired chiral alcohol, where a catalytic amount of the chiral additive is utilized.

SCHEME 3

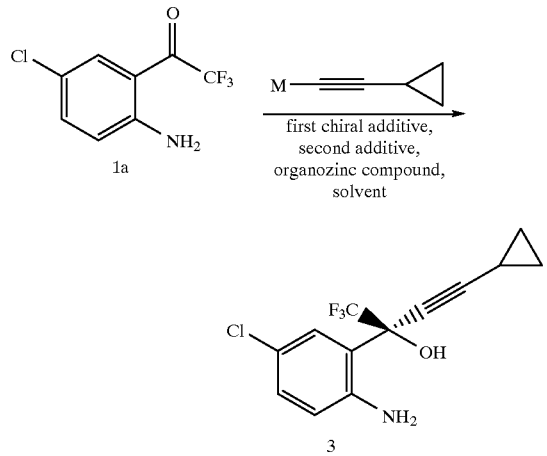

The cyclization of the amino alcohol, 3 to produce the 1,4-dihydro-2H-3,1-benzoxazin-2-one, 4 is outlined in Scheme 4 below. The reaction can be carried out as a one-step process, or alternatively a two step process with the potential isolation of the intermediate carbamate, 5 depending upon the chloroformate utilized. It has been demonstrated that the aryl chloroformates form less stable carbamates such that when they are treated with aqueous base they cyclize to the product, in a one-step process. The alkyl chloroformate, alternatively, provides an alkyl carbamate, a key intermediate capable of being isolated and purified prior to carrying out the cyclization step. Based upon the stability of the alkyl carbamates, a viable two step process for the preparation of DMP-266 has been developed which comprises the formation of the alkyl carbamate intermediate, 5 followed by the cyclization of the carbamate to give the desired product, 4. Additionally, it has been demonstrate that phosgene can also be used.

It should be noted that use of material obtained by the process of the instant invention, will require an additional equivalent of base. The amino alcohol with enhanced optical purity is isolated as the acid addition salt, and will require breaking the amine salt before carrying out the cyclization step. This has been accomplished by simply using an additional equivalent of base in the cyclization step.

SCHEME 4

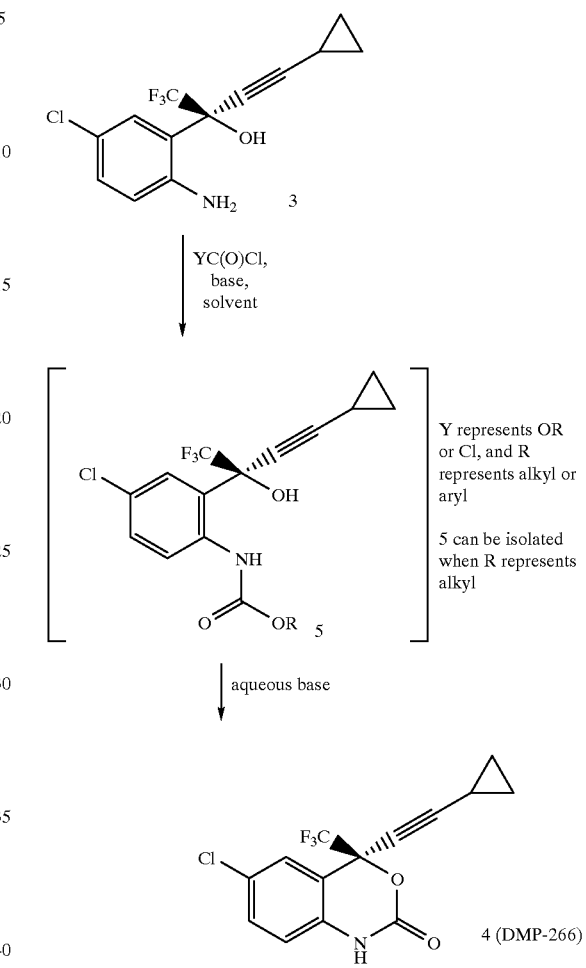

The following examples are meant to be illustrative of the present invention. These examples are presented to exemplify the invention and are not to be construed as limiting the scope of the invention.

EXAMPLE 1

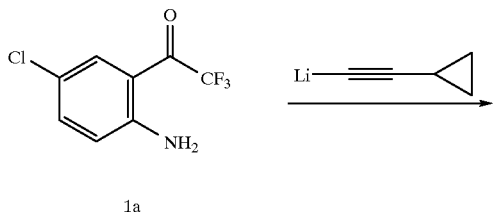

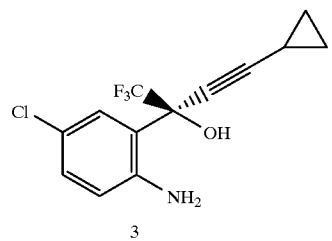

| | FW | g | mL | mmol | equiv |
|---|---|---|---|---|---|
| Ketone 1a | 323.58 | 4.48 | | 20 | 1 |
| (1R,2S)-N-pyrrolidinyl norephedrine | 205.30 | 9.85 | | 48 | 2.4 |
| cyclopropylacetylene | 66.10 | 2.64 | | 40 | 2 |
| n-BuLi (2.5M in hexane) | 64.06 | | 16 | 40 | 2 |
| MeOH (4.94M in toluene) | | | 9.72 | 48 | 2.4 |
| ZnMe₂ (2.0M in toluene) | 32.01 | | 24 | 48 | 2.4 |
| toluene | | | 80 | | |
| 1M citric acid | | | 45 | | |

Into dry toluene (40 mL) is charged (1R,2S)-N-pyrrolidinyl norephedrine (9.85 g, 48 mmol.) and dimethylzinc (2.0M in toluene) under nitrogen. The mixture is stirred for 1 h. Methanol (9.72 mL, 48 mmol.) is added. After 0.5 h the mixture is transferred to a pre-prepared slurry of n-butyllithium (2.5M,16 mL) and cyclopropylacetylene (2.64 g., 40 mmol.) in toluene (40 mL) via cannula. A solution of ketone 1a (4.48 g 20 mmol.) is added after 0.5 h. The mixture is stirred for 7 h. Aqueous work up and crystallization gives 4.8 g white solid (83% isolated yield and 83% enantiomeric excess).

EXAMPLE 2

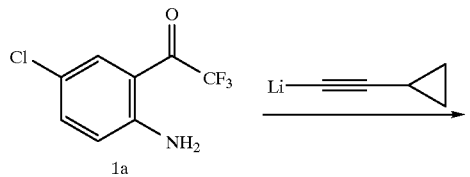

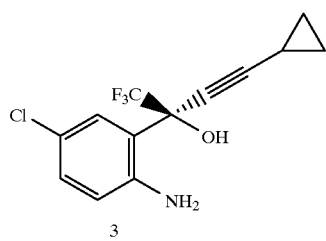

Following the procedure outlined in Example 1 above using the first chiral additive noted below in place of (1R,2S)-N-pyrrolidinyl norephedrine, the following assay yields and enantiomeric excesses were obtained:

| first chiral additive | assay yield | enantiomeric excess |
|---|---|---|
| N-methyl ephedrine | 90 | 83 |
| ephedrine | 94 | 28.2 |
| N,N-dibenzyl norephedrine | 95 | 10.4 |
| norephedrine | 25.5 | 41.6 |
| diethyl tartrate | 26.2 | −4 |
| pyrrolidinemethanol | 30 | 16.8 |
| (1R,2R)-pseudoephedrine | 63.3 | 29.8 |
| cinchonine | 90 | −11.2 |
| (1S,2S)-N-methylpseudoephedrine | 28.6 | −43 |

EXAMPLE 3

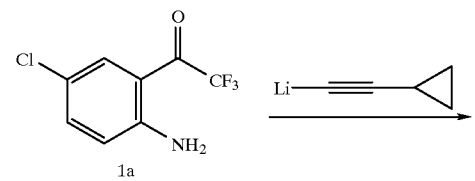

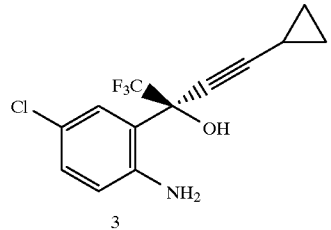

Following the procedure outlined in Example 1 above using as the first chiral additive, (1R,2S)-N-pyrrolidinyl norephedrine, with the second additives noted below in place of methanol, the following % enantiomeric excesses were obtained:

| second additive | enautiomeric excess |
|---|---|
| EtOH | 55 |
| i-PrOH | 69 |
| CF₃CO₂H | 76.2 |

Following the procedure outlined in Example 1 above using the first chiral additive, (1R,2S)-N-pyrrolidinyl norephedrine, n-butyl magnesium chloride instead of n-butyl lithium, and the second additive noted below with the reaction run at room temperature, the chiral amino alcohol was produced in the % enantiomeric excess as follows:

| second additive | enantiomeric excess |
|---|---|
| MeOH | 87 |
| t-BuOH | 89.8 |
| (CH₃)₃CCH₂OH | 95.6 |
| (CH₃)₃CCH₂OH | 94* |
| (CH₃)₃CCH(CH₃)OH | 89 |
| Ph₃COH | 74.4 |
| Cl₃CCH₂OH | 96 |
| F₃CCH₂OH | 95.7 |
| CH₂=CHCH₂OH | 90 |
| PhCH₂OH | 89 |
| (CH₃)₂NCH₂CH₂OH | 78.2 |
| 4-NO₂-phenol | 89 |
| CH₃CO₂H | 82 |

-continued

| second additive | enantiomeric excess |
|---|---|
| $CF_3CO_2H$ | 89.4 |
| $(CH_3)CCO_2H$ | 71.6 |

*The reaction temperature was 40° C.

EXAMPLE 5

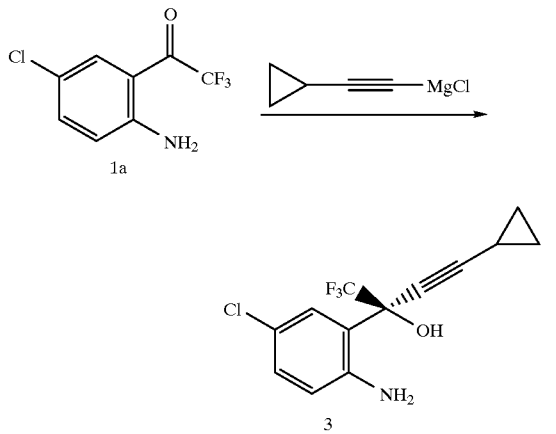

Following the procedure outlined in Example 4 above using (1S,2S)-N-methyl ephedrine as the first chiral additive in place of (1R,2S)-N-pyrrolidinyl norephedrine, and the second additive is $(CH_3)_3CCH_2OH$, the chiral amino alcohol was produced in an enantiomeric excess of 65.8%.

EXAMPLE 6

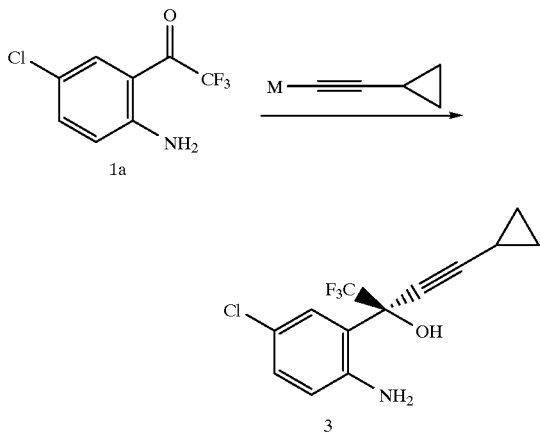

Following the procedure outlined in Example 4 above using the metal noted below in place of lithium, the following assay yields and enantiomeric excesses were obtained:

| M | assay yield | enantiomeric excess |
|---|---|---|
| MgCl | 96 | 87 |
| MgBr | 95 | 53.6 |
| MgI | 76.6 | 50.6 |

EXAMPLE 7

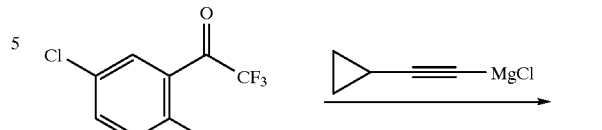

| Materials | Amount | mMol | MW |
|---|---|---|---|
| Ketone 1a | 18.63 g | 83 | 323.58 |
| (1R,2S)-N-pyrrolidinyl norephedrine 3 | 24.64 g | 120 | 205.30 |
| Cyclopropyl acetylene 2 | 6.70 g | 100 | 66.10 |
| n-BuMgCl (2.0M in THF) | 50 mL | 100 | |
| Neopentyl alcohol (99%) | 7.12 g | 80 | 88.15 |
| ZnMe₂ (2.0M in toluene) | 50 mL | 100 | |
| THF | 100 mL | | |
| 1M Citric Acid | 200 mL | | |

| Materials | Amount | mMol | MW |
|---|---|---|---|
| Ketone 1a | 18.63 g | 83 | 323.58 |
| (1R, 2S)-N-pyrrolidinyl norephedrine 3 | 24.64 g | 120 | 205.30 |
| Cyclopropyl acetylene 2 | 6.70 g | 100 | 66.10 |
| n-BuMgCl (2.0M in THF) | 50 mL | 100 | |
| Neopentyl alcohol (99%) | 7.12 g | 80 | 88.15 |
| ZnMe₂ (2.0M in toluene) | 50 mL | 100 | |
| THF | 100 mL | | |
| 1M Citric Acid | 200 mL | | |

Into an oven dried flask was charged sieves-dried THF (100 mL) and (1R, 2S)-N-pyrrolidinyl norephedrine (24.64 g, 120 mmol) under nitrogen. The mixture was cooled to −20° C. and dimethylzinc (2.0 M in toluene, 50 mL, 100 mmol) was added slowly enough to keep the temperature below 0° C. Neopentyl alcohol (7.12 g, 80 mmol) was then added after 30 min at ambient temperature. The mixture was heated at 60° C. for 1 h and cooled to room temperature. In another dry flask a solution of chloromagnesium cyclopropyl acetylide was prepared by reaction of cyclopropyl acetylene ( 6.70 g, 100 mmol) and n-butylmagnesium chloride (2.0 M in THF, 50 mL, 100 mmol). The solution was then transfered to the zinc reagent via cannula. After 20 min ketoaniline 1a (18.63 g, 8.33 mmol) was added. The reaction mixture was diluted with hexane (100 mL) and quenched with 1 N citric acid (200 mL) after 7 h. The two layers were separated. The aqueous layer was saved for norephedrine recovery. The organic layer was concentrated to ~50 mL and toluene (100 mL) was added. The solution was concentrated again to ~50 mL to remove all THF. Heptane (80 mL) was slowly added. The solid was collected by filtration and washed with heptane (30 mL) to give 22.62 g (94% yield, 96% ee) of 3 as a white solid.

EXAMPLE 8

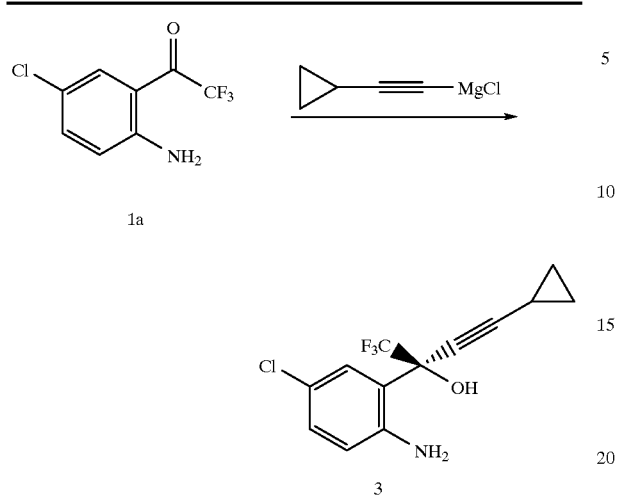

| Materials | Amount | mMol | MW |
|---|---|---|---|
| Ketone 1a | 9.32 g | 41.7 | 323.58 |
| (1R,2S)-N-pyrrolidinyl norephedrine | 12.32 g | 60 | 205.30 |
| cyclopropyl acetylene | 3.31 g | 50 | 66.10 |
| n-BuMgCl (2.0M in THF) | 25 mL | 50 | |
| neopentyl alcohol (99%) | 3.56 g | 40 | 88.15 |
| $ZnMe_2$ (2.0M in toluene) | 25 mL | 50 | |
| THF | 50 mL | | |
| 1M Citric Acid | 100 mL | | |

Into an oven dried flask was charged sieves-dried THF (50 mL) and (1R, 2S)-N-pyrrolidinyl norephedrine (12.32 g, 60 mmol) under nitrogen. The mixture was cooled to −20° C. and dimethylzinc (2.0 M in toluene, 25 mL, 50 mmol) was added slowly enough to keep the temperature below 0° C. Neopentyl alcohol (3.56 g, 40 mmol) was then added after 30 min at ambient temperature. The mixture was heated at 60° C. for 1 h and cooled to room temperature. In another dry flask a solution of chloromagnesium cyclopropyl acetylide was prepared by reaction of cyclopropyl acetylene ( 3.31 g, 50 mmol) and n-butylmagnesium chloride (2.0 M in THF, 25 mL, 50 mmol). The solution was then transferred to the zinc reagent via cannula. After 20 min the solution was cooled to 0° C. and ketoaniline 1a (9.32 g, 41.7 mmol) was added. The reaction mixture was diluted with hexane (50 mL) and quenched with 1 N citric acid (100 mL) after 48 h. The two layers were separated. The aqueous layer was saved for norephedrine recovery. The organic layer was concentrated to ~25 mL and toluene (50 mL) was added. The solution was concentrated again to ~25 mL to remove all THF. Heptane (35 mL) was slowly added. The solid was collected by filtration and washed with heptane (10 mL) to give 11.3 g (94% yield, >99% ee) of 3 as a white solid. $^1$H NMR (CDCl$_3$, 300 MHz): δ 7.52 (1 H), 7.12 (1 H), 6.61 (1 H), 4.70 (1 H), 4.39 (2 H), 1.39 (1 H), and 0.85 (4 H). $^{13}$C NMR (CDCl$_3$, 75.5 MHz) δ 143.21, 130.44, 130.04, 123.94, 123.93 (q), 121.11, 120.81, 93.51, 74.80 (q), 70.58, 88.59, and −0.85.

EXAMPLE 9

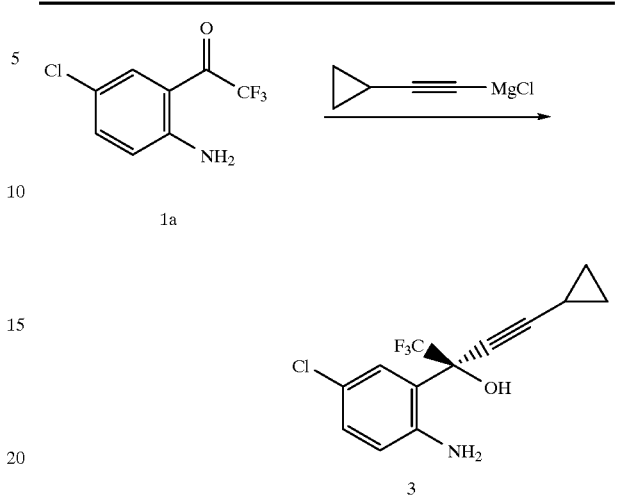

| Materials | Amount | Mol | MW |
|---|---|---|---|
| Ketone 1a | 1.00 kg | 4.47 | 223.58 |
| (1R,2S)-N-pyrrolidinyl norephedrine | 1.35 kg | 6.58 | 205.30 |
| cyclopropyl acetylene | 361.9 g | 5.47 | 66.10 |
| n-BuMgCl (2.0 M in THF) | 2.68 L | 5.37 | |
| trifluoroethanol (99%) | 429.5 g | 4.29 | 100.04 |
| $ZnEt_2$ (0.892 M in hexane) | 6.02 L | 5.37 | |
| THF | 9.36 L | | |
| 30% $K_2CO_3$ | 550 mL | | |
| 30% Citric Acid | 2.0 L | | |
| Toluene (for crystallization, 2 mL/g of 4) | 2.6 L | | |
| Heptane (for crystallization, 4 mL/g of 4) | 5.2 L | | |

To a solution of trifluoroethanol and (1R, 2S)-N-pyrrolidinyl norephedrine in THF (9 L) under nitrogen is added a solution of diethylzinc in hexane at 0° C. slowly enough to keep the temperature below 30° C. The mixture is stirred at room temperature for 0.5~1 h. In another dry flask a solution of chloromagnesium cyclopropyl acetylide is prepared as follows: To neat cyclopropyl acetylene at 0° C. is added a solution of n-butylmagnesium chloride slowly enough to keep the internal temperature ≦30° C. The solution is stirred at 0° C. for ~40 min and transfered to the zinc reagent via cannula with 0.36 L of THF as a wash. The mixture is cooled to −10° C. and ketoaniline 1a is added. The mixture is stirred at −2 to −8° C. for 35 h, warmed to room temperature, stirred for 3 h, and quenched with 30% potassium carbonate over 1.5 h. The mixture is stirred for 4 h and the solid is removed by filtration and washed with THF (2 cake volume). The wet solid still contains ~18 wt % of pyrrolidinyl norephedrine and is saved for further study. The filtrate and wash are combined and treated with 30% citric acid. The two layers are separated. The organic layer is washed with water (1.5 L). The combined aqueous layers are extracted with 2.5 L of toluene and saved for norephedrine recovery. The toluene extract is combined with the organic solution and is concentrated to ~2.5 L. Toluene is continuously fed and distilled till THF is not detectable by GC. The final volume is controlled at 3.9 L. Heptane (5.2 L) is added over 1 h. The slurry is cooled to 0° C., aged for 1 h, and filtered. The solid is washed with heptane (2 cake volume) and dried to give 1.234 Kg (95.2% yield) of amino alcohol 3 as a white crystalline. The material is 99.8 A% pure and 99.3% ee.

EXAMPLE 10

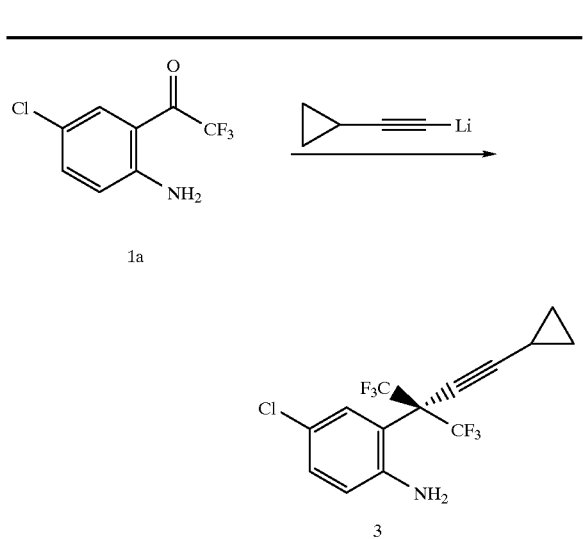

| Materials | Amount | mMol | MW |
|---|---|---|---|
| Ketone 1a | 1.68 g | 7.0 | 323.58 |
| (1R,2S)-N-pyrrolidinyl norephedrine | 0.18 g | .88 | 205.30 |
| cyclopropyl acetylene | 0.66 g | 10 | 66.10 |
| n-BuLi (2.5M in hexane) | 4.0 mL | 10 | |
| methanol | 0.81 mL | 20 | 32.01 |
| ZnMe₂ (2.0M in toluene) | 5.0 mL | 10 | |
| Toluene | 5 mL | | |
| 1M Citric Acid | 10 mL | | |

Into dry toluene is charged methanol and toluene. The mixture was cooled to −78° C. and dimethylzinc was added under nitrogen. The mixture was allowed to warm to room temperatureis and stirred for 1 h. (1R, 2S)-N-pyrrolidinyl norephedrine was added. After 0.5 h the mixture was mixed with a pre-prepared slurry of n-Butyllithium and cyclopropylacetylene in toluene (40 mL) via cannula. Ketone 1 was added after 0.5 h. The mixture is stirred for 7 h.and quenched with excess 1 M citric acid. Assay of the organic solution indicated 83% yield and 20% ee.

EXAMPLE 11

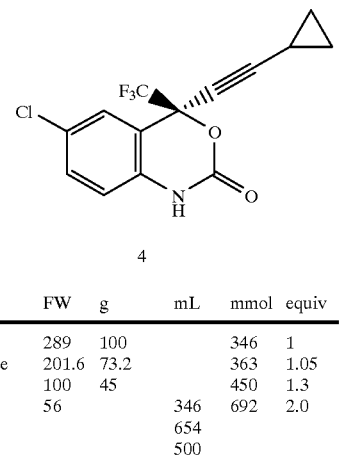

| | FW | g | mL | mmol | equiv |
|---|---|---|---|---|---|
| amino alcohol 3 | 289 | 100 | | 346 | 1 |
| 4-nitrophenylchloroformate | 201.6 | 73.2 | | 363 | 1.05 |
| KHCO₃ | 100 | 45 | | 450 | 1.3 |
| 2N KOH | 56 | | 346 | 692 | 2.0 |
| H₂O | | | 654 | | |
| MTBE | | | 500 | | |

To a three necked round bottom flask, equipped with a mechanical stirrer, nitrogen line, and thermocouple, was charged the solid amino alcohol 3, MTBE (500 mL), and aqueous KHCO₃ (45 g in 654 mL H₂O). Solid 4-nitrophenyl chloroformate was added, in 4 batches, at 25° C. During the addition the solution pH was monitored. The pH was maintained between 8.5 and 4 during the reaction and ended up at 8.0. The mixture was stirred at 20–25° C. for two hours. Aqueous KOH (2N) was added over 20 minutes, until the pH of the aqueous layer reached 11.0.

The layers were separated and 500 mL brine was added to the MTBE layer. 0.1 N Acetic acid was added until the pH was 6–7. The layers were separated and the organic phase was washed with brine (500 mL). At this point the mixture was solvent switched to EtOH/IPA and crystallized as recited in Examples 13 and 14.

EXAMPLE 12A

| | FW | g | mL | mmol | equiv |
|---|---|---|---|---|---|
| amino alcohol 3a | 289 | 100 | | 346 | 1 |
| phosgene (20 wt % in toluene) | 99 | 41 | 216 | 415 | 1.2 |

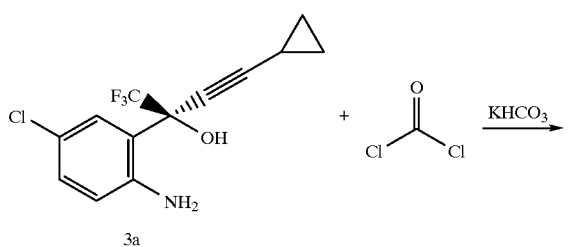

| | FW | g | mL | mmol | equiv |
|---|---|---|---|---|---|
| KHCO₃ | 100 | 86.5 | | 865 | 2.5 |
| H₂O | | | 500 | | |
| Toluene | | | 500 | | |

To a three necked round bottom flask, equipped with a mechanical stirrer, nitrogen line, and thermocouple, was charged the solid amino alcohol 3a, toulene (500 mL), and aqueous KHCO₃ (86.5 g in 500 mL H₂O). Phosgene solution in toulene was added at 25° C., and the mixture was stirred at 20–25° C. for two hours.

The layers were separated and the organic phase was washed with brine (500 mL). At this point the mixture was solvent switched to EtOH/IPA and crystallized as recited in Examples 13 and 14.

EXAMPLE 12B

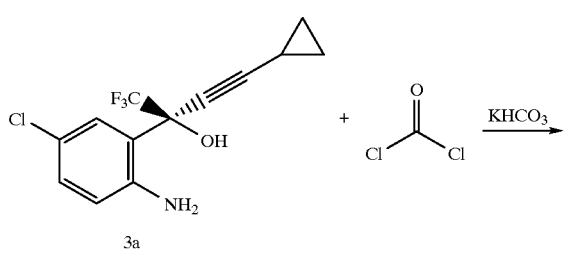

| | FW | g | mL | mmol | equiv |
|---|---|---|---|---|---|
| amino alcohol 3a | 289 | 100 | | 346 | 1 |
| phosgene (gas) | 99 | | | | |

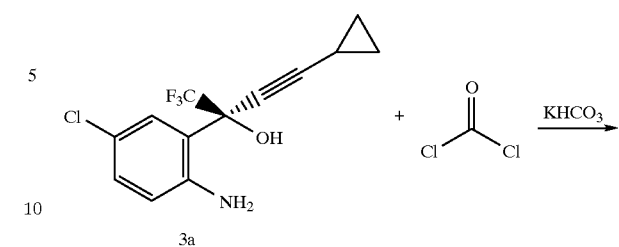

| | FW | g | mL | mmol | equiv |
|---|---|---|---|---|---|
| KHCO₃ | 100 | 86.5 | | 865 | 2.5 |
| H₂O | | | 500 | | |
| MTBE | | | 500 | | |

To a three necked round bottom flask, equipped with a mechanical stirrer, nitrogen line, and thermocouple, was charged the solid amino alcohol 3a, MTBE (500 mL), and aqueous KHCO₃ (86.5 g in 500 mL H₂O). Phosgene gas was slowly passed into the solution at 25° C., until the reaction was complete.

The layers were separated and the organic phase was washed with brine (500 mL). At this point the mixture was solvent switched to EtOH/IPA and crystallized as recited in Examples 13 and 14.

EXAMPLE 13

Crystallization of DMP-266 from 30% 2-Propanol in Water using a ratio of 15 ml solvent per gram DMP-266 Using Controlled Anti-Solvent Addition on a 400 g Scale.

400 g. of DMP-266 starting material is dissolved in 1.8 L of 2-propanol. The solution is filtered to remove extraneous matter. 1.95 L of deionized (DI) water is added to the solution over 30 to 60 minutes. 10 g. to 20 g. of DMP-266 seed (Form II wetcake) is added to the solution. The seed bed is aged for 1 hour. The use of Intermig agitators is preferred to mix the slurry. If required (by the presence of extremely long crystals or a thick slurry), the slurry is wet-milled for 15–60 seconds. 2.25 L of DI water is added to the slurry over 4 to 6 hours. If required (by the presence of extremely long crystals or a thick slurry), the slurry is wet-milled for 15–60 seconds during the addition. The slurry is aged for 2 to 16 hours until the product concentration in the supernatant remains constant. The slurry is filtered to isolate a crystalline wet cake. The wet cake is washed with 1 to 2 bed volumes of 30% 2-propanol in water and then twice with 1 bed volume of DI water each. The washed wet cake is dried under vacuum at 50° C.

EXAMPLE 14

Crystallization of DMP-266 from 30% 2-Propanol in Water using a ratio of 15 ml solvent per gram DMP-266 Using a Semi-Continuous Process on a 400 g Scale.

400 g. of DMP-266 starting material is dissolved in 1.8 L of 2-propanol. A heel slurry is produced by mixing 20 g. of Form II DMP-266 in 0.3 L of 30% (v/v) 2-propanol in water or retaining part of a slurry from a previous crystallization in the crystallizer. The dissolved batch and 4.2 L of DI water are simultaneously charged to the heel slurry at constant rates over 6 hours to maintain a constant solvent composition in the crystallizer. Use of Intermig agitators during the crystallization is preferred. During this addition the slurry is wet-milled when the crystal lengths become excessively long or the slurry becomes too thick. The slurry is aged for 2 to 16 hours until the product concentration in the supernatant remains constant. The slurry is filtered to isolate a crystalline wet cake. The wet cake is washed with 1 to 2 bed volumes of 30% 2-propanol in water and then twice with 1 bed volume of DI water each. The washed wet cake is dried under vacuum at 50° C.

EXAMPLE 15

2R-[1-hydroxy-1-trifluoromethyl-3-cyclopropylpropyn-2-yl]-4-chloroaniline hydrochloride

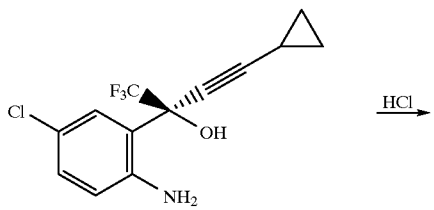

| Materials | Amount | mMol | MW |
|---|---|---|---|
| Amino alcohol (98.4% ee) | 10 g | 34.5 | 289.7 |
| 4.25 N HCl in IPA | 8.5 mL | 36.1 | 36.5 |
| IPAc | 250 mL | | |

To a solution of amino alcohol in IPAc (150 mL) at ambient temperature is charged HCl in IPA dropwise, forming a white slurry. The slurry is concentrated in vacuum to ~100 mL, during which it is flushed with 2×50 mL of IPAc. The slurry is aged at ambient temperature for 18 h and filtered. The wet cake is washed with heptane (10 mL) and dried to give 11.0 g (97.7% recovery, 99.8% ee) of the amino alcohol•HCl salt as white solid.

EXAMPLE 16

2R-[1-hydroxy-1-trifluoromethyl-3-cyclopropylpropyn-2-yl]-4-chloroaniline hydrochloride

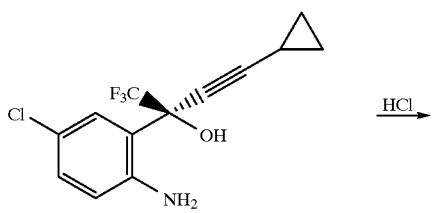

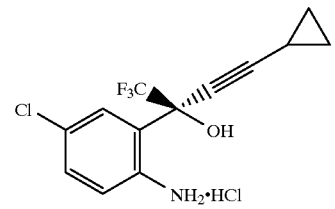

| Materials | Amount | mMol | MW |
|---|---|---|---|
| Amino alcohol (96% ee) | 10.4 g | 35.9 | 289.7 |
| 12 N aq HCl | 3.29 mL | 39.5 | 36.5 |
| IPAc | 250 mL | | |

To a solution of amino alcohol in IPAc (150 mL) at ambient temperature is added aq HCl dropwise, forming a white slurry. The slurry is concentrated in vacuum to ~100 mL, during which it is flushed with 2×50 mL of IPAc. The slurry is aged at ambient temperature for 24 h and filtered. The wet cake is washed with cold IPAc (30 mL) and dried to give 10.5 g (90% recovery, 100% ee) of the amino alcohol•HCl salt as white solid.

EXAMPLE 17

2R-[1-hydroxy-1-trifluoromethyl-3-cyclopropylpropyn-2-yl]-4-chloroaniline hydrobromide

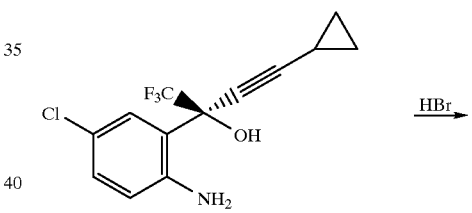

| Materials | Amount | mMol | MW |
|---|---|---|---|
| Amino alcohol (96% ee) | 10.4 g | 35.9 | 289.7 |
| 48% aq HBr | 4.1 mL | 35.9 | 81 |
| Toluene | 210 mL | | |
| THF | 15 mL | | |

To a solution of amino alcohol in Toluene (150 mL) and THF (50 mL) at ambient temperature is added aq HBr dropwise, forming a clear solution. The solution is concentrated in vacuum to ~120 mL, to give a slurry. The volume was adjusted with toluene to approx 140 mL and then 15 mL THF was added. The slurry is aged at ambient temperature for 10 h and filtered. The wet cake is washed with toluene (30 mL) and dried to give 12.35 g (95% recovery, 99.6% ee) of the amino alcohol•HBr salt as white solid.

EXAMPLE 18

2R-[1-hydroxy-1-trifluoromethyl-3-cyclopropylpropyn-2-yl]-4-chloroaniline hydrobromide

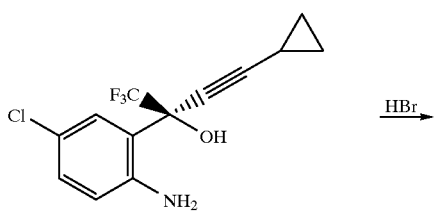

| Materials | Amount | mMol | MW |
|---|---|---|---|
| Amino alcohol (96% ee) | 10.4 g | 35.9 | 289.7 |
| 48% aq HBr | 4.1 mL | 35.9 | 81 |
| IPAC | 200 | | |

To a solution of amino alcohol in IPAC (200 mL) at ambient temperature is added aq HBr dropwise, forming a clear solution. The solution is concentrated in vacuum to ~100 mL, to give a slurry. The slurry is aged at ambient temperature for 10 h and filtered. The wet cake is washed with cold IPAC (30 mL) and dried to give 12.35 g (95% recovery, 99.3% ee) of the amino alcohol•HBr salt as white solid.

EXAMPLE 19

2R-[1-hydroxy-1-trifluoromethyl-3-cyclopropylpropyn-2-yl]-4-chloroaniline hydrochloride

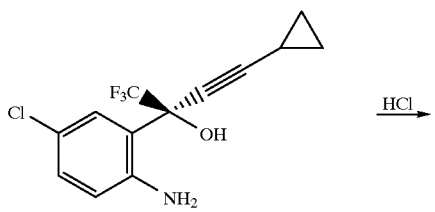

| Materials | Amount | mMol | MW |
|---|---|---|---|
| Amino alcohol (99.3% ee) | 5.78 g | 20 | 289.7 |
| 6N HCl | 3.67 mL | 22 | 36.5 |
| IPAc | 50 mL | | |

To a solution of amino alcohol in IPAc (50 mL) at ambient temperature is charged 6 N HCl dropwise to give a solution. The solution was concentrated in vacuum to ~50 mL during which it was flushed with 2×50 mL of IPAc. The resultant slurry was aged at ambient temperature for 12 h and filtered. The wet cake was washed with 15 mL IPAc/heptane (1/2) and dried to give 6.31 g (99.9%ee, 97.5% recovery) of the HCL salt as white solids.

EXAMPLE 20

2R-[1-hydroxy-1-trifluoromethyl-3-cyclopropylpropyn-2-yl]-4-chloroaniline hemisulfate

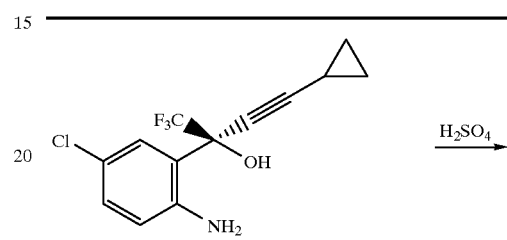

| Materials | Amount | mMol | MW |
|---|---|---|---|
| Amino alcohol (96% ee) | 5.2 g | 18 | 289.7 |
| 50 W % H$_2$SO$_4$ | 1.76 g | 20 | 98 |
| IPAc | 100 mL | | |

To a solution of amino alcohol in IPAc (100 mL) at ambient temperature is charged 50 W % H2SO4 dropwise to give a solution. The solution was concentrated in vacuum to ~50 mL during which it was flushed with 2×50 mL of IPAc. The resultant slurry was aged at ambient temperature for 12 h and filtered. The wet cake was washed with 15 mL of cold IPAc and dried to give 4.20 g (99.9%ee, 72% recovery) of the hemisulfate salt as white solids.

EXAMPLE 21

2R-[1-hydroxy-1-trifluoromethyl-3-cyclopropylpropyn-2-yl]-4-chloroaniline hydrochloride

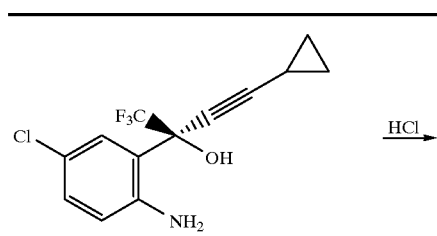

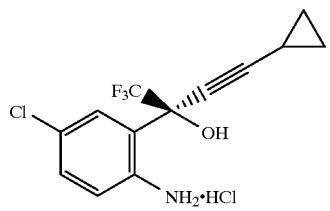

| Materials | Amount | mMol | MW |
|---|---|---|---|
| Amino alcohol (97.6% ee) | 11.5 g | 39.7 | 289.7 |
| 12N HCl | 3.64 mL | 43.7 | 36.5 |
| IPAc | 50 mL | | |

To a solution of amino alcohol in a mixture of THF, heptane and toluene (150 mL) at ambient temperature is charged 6 N HCl dropwise to give a solution. The solution was concentrated in vacuum to ~70 mL during which it was flushed with 2×50 mL of IPAc. The resultant slurry was aged at ambient temperature for 12 h and filtered. The wet cake was washed with 30 mL IPAc/heptane (1/2) and dried to give 11.8 g (99.9%ee, 92% recovery) of the HCl salt as white solids.

What is claimed is:

1. A process for enhancing the optical purity of the R-amino alcohol of formula:

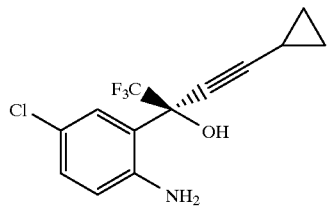

comprising the steps of:
(a) adding slowly an acid solution or gas to a solution of the amino alcohol in an organic solvent to form a slurry of the acid addition salt of the amino alcohol;
(b) concentrating the slurry of the amino alcohol acid addition salt of the amino alcohol;
(c) flushing the concentrated slurry of the amino alcohol acid addition salt with organic solvent to adjust the solvent composition;
(d) aging the slurry of the amino alcohol acid addition salt at ambient temperature for about 2 hours to about 24 hours;
(e) filtering the aged slurry of the amino alcohol acid addition salt to isolate a wetcake of the amino alcohol acid addition salt;
(f) washing the wetcake of the amino alcohol acid addition salt with cold organic solvent; and
(g) drying the wetcake of the amino alcohol acid addition salt to isolate the amino alcohol acid addition salt as a solid with enhanced optical purity.

2. The process for enhancing the optical purity of the R-amino alcohol as recited in claim 1, wherein the acid has a pKa of less than or equal to 3.

3. The process for enhancing the optical purity of the R-amino alcohol as recited in claim 2, wherein the organic solvent is selected from the group consisting of: isopropyl acetate, ethyl acetate, toluene, methyl t-butyl ether, acetonitrile, tetrahydrofuran, methanol, ethanol, isopropanol, hydrocarbon solvents, and mixtures therefrom.

4. The process for enhancing the optical purity of the R-amino alcohol as recited in claim 3, wherein the acid has a pKa of less than or equal to 1.

5. The process for enhancing the optical purity of the R-amino alcohol as recited in claim 4, wherein the organic solvent is selected from the group consisting of: isopropyl acetate, ethyl acetate, toluene, methyl t-butyl ether, acetonitrile, tetrahydrofuran, methanol, ethanol, isopropanol, hydrocarbon solvent, and mixtures therefrom.

6. The process for enhancing the optical purity of the R-amino alcohol as recited in claim 5, wherein the acid is selected from the group consisting of: HX, where X is defined as halide (Cl, Br, I, or F), $H_2SO_4$, trifluoroacetic acid, trichloroacetic acid, $RSO_3H$, where R represents ($C_1$–$C_6$)-alkyl, ($C_2$–$C_6$)-alkenyl, ($C_2$–$C_6$)-alkynyl, aryl which is defined as phenyl or naphthyl and heteroaryl which is defined as 5 or 6-membered ring substituted with one or two heteroatoms selected from O, S, N, and ($C_1$–$C_6$)-alkyl, ($C_2$–$C_6$)-alkenyl, ($C_2$–$C_6$)-alkynyl, aryl or heteroaryl can be substituted or unsubstituted with one, two or three substituents selected from the group consisting of: Br, Cl, F, I, ($C_1$–$C_6$)-alkyl, ($C_2$–$C_6$)-alkenyl, ($C_2$–$C_6$)-alkynyl, ($C_1$–$C_6$)-alkoxy, cyano, nitro, hydroxy, CHO, $CO_2H$, $SO_3H$, $COC_1$–$C_6$-alkyl, $CO_2C_1$–$C_6$-alkyl, $CONR^1R^2$, $NR^1R^2$, $NR^1COC_1$–$C_6$-alkyl, wherein $R^1$ and $R^2$ are independently defined as: halo (Cl, Br, F, I), $CF_3$, CN, $NO_2$, $NH_2$, $NH(C_1$–$C_6$-alkyl), $N(C_1$–$C_6$-alkyl)$_2$, $CONH_2$, CONH ($C_1$–$C_6$-alkyl), $CON(C_1$–$C_6$-alkyl)$_2$, $NHCONH_2$, $NHCONH(C_1$–$C_6$-alkyl), $NHCON(C_1$–$C_6$-alkyl)$_2$, $CO_2$-$C_1$–$C_6$-alkyl, $C_1$–$C_6$-alkyl, $C_2$–$C_6$-alkenyl, $C_2$–$C_6$-alkynyl, $C_3$–$C_7$-cycloalkyl, or $C_1$–$C_6$-alkoxy, such that $C_1$–$C_6$-alkyl is unsubstituted or substituted with aryl, aryl is defined as phenyl or naphthyl, unsubstituted or substituted with $C_1$–$C_6$-alkyl, $C_1$–$C_6$-alkoxy, $NO_2$, or halo (Cl, Br, F, I).

7. The process for enhancing the optical purity of the R-amino alcohol as recited in claim 6, wherein the organic solvent is selected from the group consisting of: isopropyl acetate, ethyl acetate, toluene, methyl t-butyl ether, acetonitrile, tetrahydrofuran, methanol, ethanol, isopropanol, and hydrocarbon solvents, and mixtures therefrom.

8. The process for enhancing the optical purity of the R-amino alcohol as recited in claim 7, wherein the acid solution or gas is selected from the group consisting of: 1,5 naphthalenedisulfonic acid, p-toluenesulfonic acid, $CH_3SO_3H$, triflic acid, and camphorsulfonic acid HCl, HBr, and $H_2SO_4$.

9. The process for enhancing the optical purity of the R-amino alcohol as recited in claim 8, wherein the acid solution or gas and organic solvent are: HCl and isopropyl acetate, HBr and isopropyl acetate or HBr and a toluene-tetrahydrofuran mixture.

* * * * *